(12) United States Patent
Kawai

(10) Patent No.: US 6,589,912 B2
(45) Date of Patent: Jul. 8, 2003

(54) COMPOSITION FOR BEING SPRAYED ON FOLIAGE OF PLANT AND USE OF THE SAME

(76) Inventor: Hiroshi Kawai, 25-3-305, Nakatahigashi 2-chome, Izumi-ku, Yokohama-shi, Kanagawa-ken (JP)

(*) Notice: Subject to any disclaimer, the term of this patent is extended or adjusted under 35 U.S.C. 154(b) by 0 days.

(21) Appl. No.: 09/751,188

(22) Filed: Dec. 29, 2000

(65) Prior Publication Data

US 2002/0137632 A1 Sep. 26, 2002

(51) Int. Cl.[7] ............................................. A01N 59/16
(52) U.S. Cl. .................................... 504/120; 504/121
(58) Field of Search .............................. 504/120, 121

(56) References Cited

U.S. PATENT DOCUMENTS

| | | | | |
|---|---|---|---|---|
| 4,219,392 A | * | 8/1980 | Halmann | 204/72 |
| 5,759,948 A | * | 6/1998 | Takaoka et al. | 502/325 |
| 6,110,867 A | | 8/2000 | Glenn et al. | 504/119 |

FOREIGN PATENT DOCUMENTS

| | | | |
|---|---|---|---|
| JP | 54-015828 | | 6/1979 |
| JP | 3-228639 | | 10/1991 |
| JP | Hei 6-209985 | | 8/1994 |
| JP | Hei 8-47687 | | 2/1996 |
| JP | 09-087121 | | 3/1997 |
| JP | 10-272355 | * | 10/1998 |
| JP | 11-343209 | | 12/1999 |
| JP | 2000 287544 | | 10/2000 |
| JP | 2001-10914 | * | 1/2001 |
| SU | 1630742 A1 | | 2/1991 |
| WO | WO 98/51155 | | 11/1998 |

OTHER PUBLICATIONS

"Characterization of a Novel Trypanosome Lytic Factor from Human Serum", Jayne Raper et al., *Infection and Immunity*, vol. 67, No. 4, Apr. 1999, pp. 1910–1916 (corresponding to JP 54–015828 cited above).

* cited by examiner

*Primary Examiner*—S. Mark Clardy
(74) *Attorney, Agent, or Firm*—Weingarten, Schurgin, Gagnebin & Lebovici LLP

(57) ABSTRACT

A composition for being sprayed on the foliage of a plant, which is suspended in water so as to apply to the foliage of the plant by using a paint sprayer or the like, which provides the effects that the photodecomposition of water on the surface of the foliage is advanced, and thereby carbon dioxide assimilation in the plant can be expedited, and an oxygen free radical as produced in a process of a photodecomposition reaction of water can be used for a lipid peroxidation reaction in a plant cell membrane, and a bactericide, an insecticide, a growth regulator and/or a herbicide which are excessively left on the surface of the foliage can be decomposed; and a method of using the same can be provided. A composition for being sprayed on the foliage of a plant, comprising at least one semiconductor photocatalyst(s) as an active ingredient, wherein, if necessary, further comprises at least one carbonate(s) and/or hydrogencarbonate(s) is used. The composition is sprayed on the above-ground part of the plant.

5 Claims, 3 Drawing Sheets

Dynamic protection mechanism of plants against plant disease-causing bacteria

US 6,589,912 B2

COMPOSITION FOR BEING SPRAYED ON FOLIAGE OF PLANT AND USE OF THE SAME

BACKGROUND OF THE INVENTION

1. Field of the Invention

The present invention relates to a composition for being sprayed on the foliage of a plant, in which a semiconductor photocatalyst is included as an essential component; and a use of the same.

2. Detailed Description of the Prior Art

The decrease of carbon dioxide assimilation (e.i., photosynthesis) in a field crop directly means that a harvesting is decreased. Conventionally, in an agricultural land, in order to have a good harvest, a massive commitment of fertilizers, a carbon dioxide treatment and the like have been carried out, and thereby some effects have been provided; however, when an amount of sunshine was insufficient due to an environmental factor such as weather, on the contrary, such treatments sometimes affected harvests.

Furthermore, in order to control an excess luxuriant growth of the foliage of a plant, an auxin based hormone agent, a gibberellin biosynthesis inhibitor, an ethylene producing agent and the like are sometimes used; however, it is the present states of things that a lot of them are apt to cause a chemical injury to a plant, and provide even a human body with a high toxicity.

Besides, as a countermeasure against diseases causing great damage to field crops, novel bactericides which took years before development have been brought to market practically every year; however, even when any novel bactericide is used, a drug-resistant bacteria occurs in several short years, thus effects often come not to be provided as expected. Therefore, it has been hurried to develop a method of controlling diseases, which is quite different in function therefrom.

In particular, in recent years, an agricultural chemicals residue and/or a dioxin in field crops constitutes a social problem; however, as a method of removing these toxic or deleterious substances before a consumer practically eats a crop, there is no effective manner except washing, which is in a problem.

On the other hand, basic research on photodecomposition of water wherein a semiconductor photocatalyst is used has been carried out from a long time; in recent years, a tile in which titanium oxide is used (refer to Japanese Patent Laid-Open Publication No.209985/94), an apparatus for purifying water (refer to Japanese Patent Laid-Open Publication No.47687/96), and the like are put to practical use. The property that when a semiconductor photocatalyst has received light energy larger than band-gap energy, an electrically positive valence band and an electrically negative conduction band are formed in the crystal is applied to these. When a water system in which a semiconductor photocatalyst is included is exposed to light irradiation, an oxidation reaction of water $[4H_2O(4H^+ +4OH^-)]$ as shown by the following formula ① is advanced near the valence band, while a reduction reaction of a material as shown by the following formula ② is advanced near the conduction band.

$$4OH^- \rightarrow O_2 + 2H_2O, \quad \text{the formula ①}$$

$$4H^+ \rightarrow 2H_2. \quad \text{the formula ②}$$

Furthermore, near the valence band, in a process wherein the above-mentioned reaction is advanced, hydroxyl group is oxidized into hydroxy radical (.OH), while near the conduction band, oxygen is subjected to one electron reduction, and thereby superoxide anion radical ($O_2^-$) is formed.

Besides, when carbon dioxide or carbonate ion exists in these systems, near the conduction band, a reduction reaction of $CO_2$ as shown in the following formula ③ is advanced:

$$CO_2 + nH^+ \rightarrow CO, HCHO, CH_3OH, CH_4. \quad \text{the formula ③}$$

The reaction through which this $CO_2$ is reduced is a reaction as referred to as "an artificial photosynthesis", which is studied in many research institutions. However, these research examples merely relate to researches at a basic research level, which are to the backbone concentrated on the sides of phenomena such as a partial analysis of the mechanism of photosynthesis, and a mere photodecomposition of water. Furthermore, a lot of the research examples have the problems that (1) the activity of a catalyst is very low and is not efficient; (2) a method of preparing a catalyst, or the conditions of reaction are complicated; (3) a reverse reaction is large; and the like. Thus, it is the present state of things that the above research examples are far from being put to practical use.

In an agricultural land, in order to have a good harvest, a massive commitment of a fertilizer, a herbicide, a bactericide, an insecticide and the like have been carried out, and thereby some effects have been provided; however, even at the present time when technologies have been developed, it is a serious problem for persons being engaged in agriculture how to prevent a crop as driven into an underdeveloped state when an amount of sunshine has been insufficient. Furthermore, in the midst of time when the disruption of the living organisms environment due to a chlorine compound is cried, it is of urgent necessity to develop a growth regulator and/or a method of controlling disease, which are environmental and safe.

SUMMARY OF THE INVENTION

It is a first object of the present invention to provide a composition for being sprayed on the foliage of a plant so as to solve conventional problems, wherein the composition is suspended in water so as to apply to the foliage of the plant by using a paint sprayer or the like, so that the photodecomposition of water on the surface of the foliage is advanced, and thereby carbon dioxide assimilation in the plant can be expedited, and an oxygen free radical as produced in a process of a photodecomposition reaction of water can be used for a lipid peroxidation reaction in a plant cell membrane, and the generation of ethylene, which is one of plant hormones, is expedited, and consequently, the plant growth such as the dwarf of the plant, the promotion of rooting in a capillary root thereof, the promotion of date of maturity, the formation of an abscission layer, or the induction of flower bud can be controlled, and furthermore, Phyto-alexin, which is derived by a lipid peroxidation reaction is accumulated, and thereby a disease resistance for the plant can be provided, and a bactericide, an insecticide, a growth regulator and/or a herbicide which are excessively left on the surface of the foliage can be decomposed; and it is a second object of the present invention to provide a method of using such a composition for being sprayed on the foliage of the plant.

The inventors concerned have earnestly and repeatedly studied thereabout, and consequently, it has been found that the above-mentioned problems can be solved, wherein a composition comprising a semiconductor photocatalyst providing little load to environment, as an essential ingredient, and if necessary, further comprising a carbonate and/or a hydrogencarbonate, wherein the photocatalyst can be easily prepared, and the condition of reaction is simple, is sprayed on a plant, and thereby, the photodecomposition of water on the surface of foliage can be expedited, and photosynthesis can be supplemented when an amount of sunshine was insufficient, while the growth of the plant can be controlled. Thus, the present invention has been made.

The invention claimed in claim 1 relates to a composition for being sprayed on the foliage of a plant, characterized in that said composition comprises at least one semiconductor photocatalyst(s) as an active ingredient, or if necessary, further comprises at least one carbonate(s) and/or hydrogencarbonate(s).

The invention claimed in claim 2 relates to a composition for being sprayed on the foliage of a plant according to claim 1, characterized in that the composition is used as a photosynthesis accelerator which accelerates water decomposition so as to accelerate a photosynthesis in the plant.

The invention claimed in claim 3 relates to a composition for being sprayed on the foliage of a plant according to claim 1, characterized in that the composition is used as a plant growth regulator which accelerates a lipid peroxidation reaction so as to derive ethylene, which is one of plant hormones, and thereby controls the growth of the plant.

The invention claimed in claim 4 relates to a composition for being sprayed on the foliage of a plant according to claim 1, characterized in that the composition is used as a disease-resistance providing agent which accelerates a lipid peroxidation reaction so as to derive Phyto-alexin in a plant, and thereby provides a disease resistance for the plant.

The invention claimed in claim 5 relates to a composition for being sprayed on the foliage of a plant according to claim 1, characterized in that the composition is used as a decomposing agent which accelerates water decomposition so as to produce an oxygen free radical, and thereby decomposes a bactericide, an insecticide, a growth regulator and/or a herbicide which are excessively left on the surface of the foliage.

The invention claimed in claim 6 relates to a composition for being sprayed on the foliage of a plant according to claim 1, characterized in that the composition is used as a chemical agent which has two or more effects selected from the group consisting of a photosynthesis accelerator, a plant growth regulator, a disease-resistance providing agent and a decomposing agent.

The invention claimed in claim 7 relates to a composition for being sprayed on the foliage of a plant according to any one of claims 1 to 6, characterized in that the semiconductor photocatalyst(s) is included in an amount of 0.0005 percent to 50 percent by weight of the total weight of the composition.

The invention claimed in claim 8 relates to a composition for being sprayed on the foliage of a plant according to any one of claims 1 to 7, characterized in that a weight ratio of the semiconductor photocatalyst(s) to the carbonate(s) and/or hydrogencarbonate(s) is selected from the range of 1:20000 to 1:1.

The invention claimed in claim 9 relates to a composition for being sprayed on the foliage of a plant according to any one of claims 1 to 8, characterized in that the semiconductor photocatalyst(s) is titanium oxide.

The invention claimed in claim 10 relates to a composition for being sprayed on the foliage of a plant according to claim 9, characterized in that the titanium oxide is of anatase-type.

The invention claimed in claim 11 relates to a composition for being sprayed on the foliage of a plant according to claim 9 or 10, characterized in that the average particle size of the titanium oxide is in the range of 1 nm to 500 nm.

The invention claimed in claim 12 relates to a composition for being sprayed on the foliage of a plant according to any one of claims 1 to 11, characterized in that the carbonate(s) and/or the hydrogencarbonate(s) is water soluble.

The invention claimed in claim 13 relates to a composition for being sprayed on the foliage of a plant according to claim 12, characterized in that the carbonate(s) and/or hydrogencarbonate(s) is selected from the group consisting of $Na_2CO_3$, $NaHCO_3$, $K_2CO_3$ and $KHCO_3$.

The invention claimed in claim 14 relates to a use of a composition for being sprayed on the foliage of a plant according to any one of claims 1 to 13, characterized in that the composition is sprayed on the above-ground part of the plant.

The invention claimed in claim 15 relates to a use of a composition for being sprayed on the foliage of a plant according to claim 14, characterized in that the composition is applied to the plant by diluting with water wherein the upper limit of dilution is 100,000 times.

The invention claimed in claim 16 relates to a use of a composition for being sprayed on the foliage of a plant according to claim 14 or 15, characterized in that the composition is mixed with one or more adjuvant(s) selected from the group consisting of a nonionic, anionic, cationic or amphoteric surface active agent, a fixing agent, a thickener, a suspending agent, a neutralizer, an antiseptic agent and a dust diluent so as to be applied to said plant.

The invention claimed in claim 17 relates to a use of a composition for being sprayed on the foliage of a plant according to any one of claims 14 to 16, characterized in that the composition is mixed with at least one Hill oxidant so as to be applied to said plant.

BRIEF DESCRIPTION OF THE DRAWINGS

These and other objects and advantages of the invention will become clear from the following description with the reference to the accompanying drawings, wherein.

DETAILED DESCRIPTION OF THE PREFERRED EMBODIMENT

Figure 1:
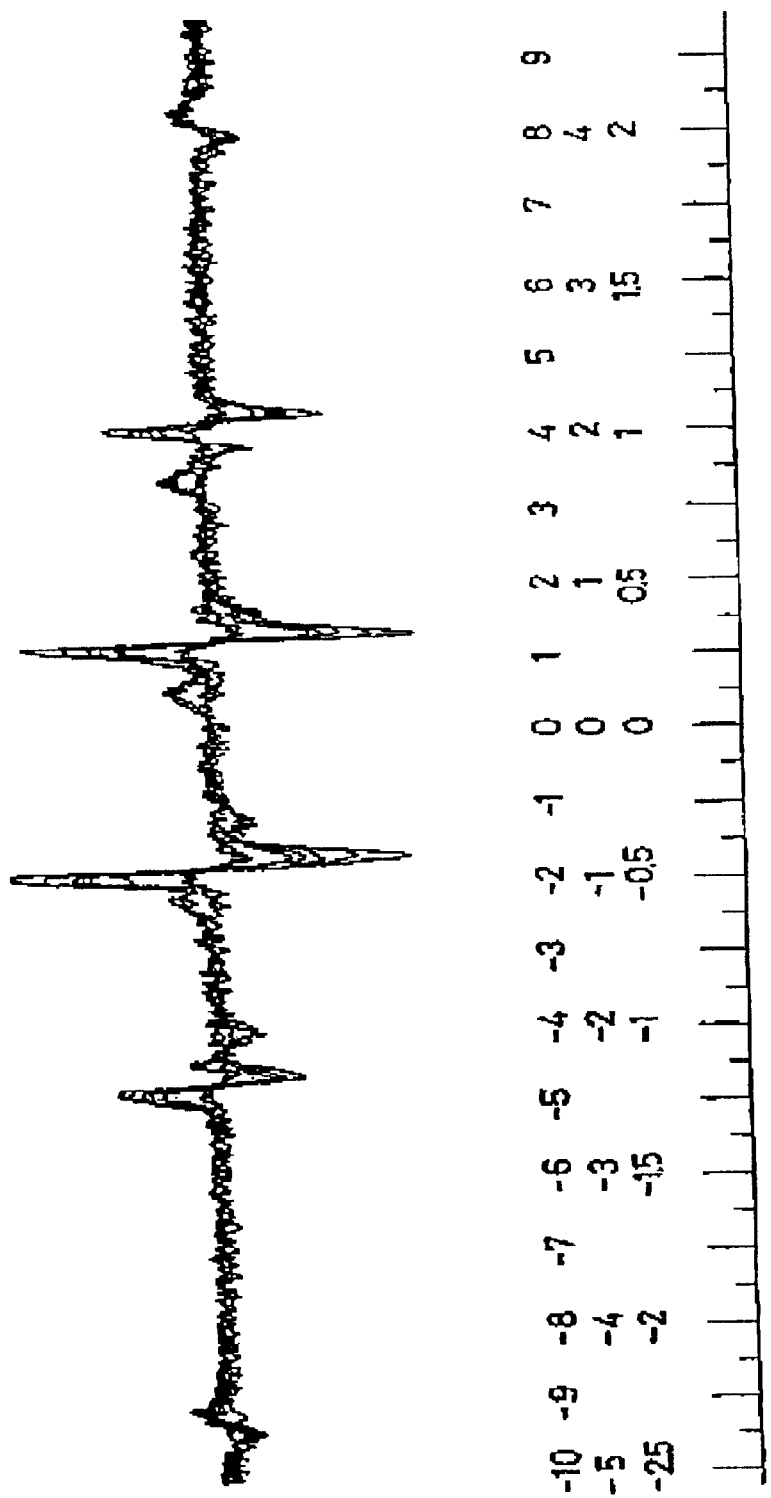
FIG. 1 shows an ESR-spectrum of each of a composition "1" for being sprayed on the foliage of a plant of the present invention, and DMPO.

Detailed description of the present invention is set forth hereafter. In a preferred embodiment, semiconductor photocatalyst(s) employed in this invention may adopt any chemical element, any form of chemical compound, but preferably may fill one or more of the adjoined four requirements:

(1) band gap of less than 4.1 eV (300 nm) facilitating utilization of solar light,
(2) stability in aqueous solution of carbonates salts and/or bicarbonate salts under the irradiation of light,
(3) electric potential of conduction band of said semiconductor photocatalyst(s) that is larger than the hydrogen-generation potential of water under the irradiation of light, (4) electric potential of valence band of said semiconductor that is larger than the oxygen-generation potential of water under the irradiation of light.

Detailed examples of semiconductor photocatalyst(s) preferred in this invention include metal oxides such as $TiO_2$, ZnO, $WO_3$, $SnO_2$, complex metal oxides containing multiple metallic elements such as $SrTiO_3$, $KTaO_3$, metal sulfides such as CdS, ZnS, metal chalcogenides such as CdSe, metal complexes such as Co complexes or Rh complexes, $[Ru(bpy)_3]^{2+}$, Si, GaP, GaAs as well as polymer-based semiconductor photocatalyst(s) bringing in any of the above items.

Some of aforementioned semiconductor photocatalyst(s) including part of metal oxides such as ZnO, metal sulfides such as ZnS, metal chalcogenides such as CdSe, are preferred to avoid their singular use. This is because they dissolve in water under the irradiation of light when employed as semiconductor photocatalyst(s) in aqueous phase, although they are equipped with a satisfactory band gap utilizable of solar light. Furthermore, metals such as Cd, Se, and As are poisonous to a human body, and should be avoided to use in practical cases.

The scope of manufacturing methods for said semiconductor photocatalyst(s) in this invention is not limited to the preferred embodiments set forth herein. The precursor substances possessing the metal active center include chlorides, oxides, sulfides, sulfates, nitrates, phosphates, organic carboxylates, or elemental metals. Methods of supporting metals on appropriate carriers may adopt any technique including an ion-exchange method, a physical mixing method, an impregnation method, and a photoelectric deposition method. Upon actual application of said semiconductor photocatalyst(s), they may be used singly or in combination with plural substances mixed in optional ratio.

The carbonate salts and bicarbonate salts used in a preferred embodiment of the invention together with said semiconductor photocatalyst(s) upon necessity are not limited to the examples and descriptions set forth herein unless they are capable of evolving carbonate ions or bicarbonate ions. More particularly, they include sodium carbonate, potassium carbonate, calcium carbonate, ammonium carbonate, sodium sesqui-carbonate, sodium bicarbonate, potassium bicarbonate, ammonium bicarbonate, potassium sesqui-carbonate, ammonium sesqui-carbonate, lithium carbonate, and lithium bicarbonate. They may be used singly or in combination with plural substances mixed in optional ratio. Furthermore, the carbonate ions and/or bicarbonate ions generated in aqueous phase by bubbling in of carbon dioxide gas may be used for the purpose.

The photosynthesis is defined as a synthetic reaction of organic compounds from carbon dioxide utilizing the energy of light. The photosynthetic reaction in the plant body may be expressed by the forthcoming Equation (1).

$$2H_2O + CO_2 \rightarrow (CH_2O) + O_2 + H_2O \quad (1)$$

Ordinarily this reaction proceeds in two steps described by the following Equations (2) and (3) under the presence of nicotinamid adenine dinucleotide phosphate (NADP) and adenosine triphosphoric acid (ATP);

$$2H_2O \rightarrow 2H_2 + O_2 \quad (2)$$

that is, the decomposition reaction of water expressed in Equation (2) coupled with $$2H_2 + CO_2 \rightarrow (CH_2O) + H_2O \quad (3)$$

the assimilation reaction of carbon dioxide expressed in Equation (3).

Application of said semiconductor photocatalyst(s) described in this invention to plants helps to reinforce the first step of said photosynthesis, as it accelerates the decomposition reaction of water according to Equation (2) under the irradiation of light. Furthermore, addition of carbonate salts and/or bicarbonate salts helps to accelerate said decomposition reaction of water in Equation (2) further as well as furnish the source of carbon dioxide for Equation (3), facilitating the particularly accelerated photosynthetic reaction.

Application of a composition for being sprayed on the foliage of a plant described in the present invention makes accelerate the generation reaction of ethylene, which is a hormone to plants, and leads resultantly to growth regulation of plants in their various phases, exemplified by dwarfed plants, growth acceleration of capillary roots, a quickened period of maturity, formation of an exfoliated layer, and induction of buds. Ethylene is known to evolve from plant bodies when the cells in the plant suffer from stress by injury, and the like. With regard to its mechanism, it is getting known in recent years that the generated oxygen free radicals work to peroxidize lipids in the cell membrane leading to generation of ethylene.

The composition for being sprayed on the foliage of a plant described in the present invention is characterized by accelerated generation of oxygen free radicals under the irradiation of light in high efficiency, and is capable of generating ethylene in high yields. Furthermore, the preferred embodiments of the present invention may allow addition of methionine, which is a precursor of ethylene, for the purpose of accelerating ethylene generation. Adding form of methionine is not limited to the examples and descriptions set forth herein. For example, usable substances include D-methionine, L-methionine, DL-methionine, and mixtures thereof. Their production methods are not particularly limited.

Phytoalexin is an anti-bacterial substance that plants synthesize themselves at infection with disease-causing bacteria. It is widely acknowledged as a protecting substance inherent to plants. Natural examples of alexins include Sakuranetin found in rice plants, Momilactone-A, Momilactone-B, a group of Oryzalexins, Lubimin and Solavetivone in eggplants, p-coumaric acid and 6-methoxybenzoxazoline in corns, Pisatin in podded peas, Griceorin in soybeans, Vetablugarin in beats, Ricitin in potatoes, 6-Methoxy-melain in carrots, Blacinin in Chinese cabbages, Ricitin in tomatoes, α-Vinypherin and Risveratrol in grapes, and Capsydiol in tobaccos.

These protecting reactions in plants start from a primary reaction in which unsaturated carboxylic acids, that are isolated from cell membrane of ordinary plants by the action of phospholipase A2, are peroxidized by the action of lipoxygenase and/or peroxidase in the plant body. Oxygen free radicals closely correlate with this peroxidation reaction of unsaturated carboxylic acids. It is getting known in recent years that treatment of a generator of oxygen free radicals to a plant leads to induction of phytoalexins.

To express in other words, the composition for being sprayed on the foliage of a plant described in the present invention is capable of promoting the formation of phytoalexins by acceleration of the peroxidation reaction of unsaturated carboxylic acids in plant bodies. This is because the composition is equipped with a quality to evolve oxygen free radicals in the course of photo-decomposition reaction of water.

It is also allowed to add elicitors to a composition for being sprayed on the foliage of a plant described in this invention for the purpose of accelerating generation of phytoalexins. Examples of these elicitors include jasmonic acid, its derivative, salicylic acid, its derivative, sulfur-containing amino acids such as methionine, cysteine, cystine and their derivatives, copper, divalent iron, ascorbic acid, and the like. However, the scope of elicitors as well as their production methods is not particularly limited to the compounds set forth herein.

Examples of anti-bacterial agents included in the present invention are Dineb, Toluchlophosmethyl, Furametopil, Diphenoconazol, Prochloraz, Befrazoate, Tetraconazol, Cresoxylmethyl, Methominostrobin, Mevanypyrim, Cyprodinil, a series of sulfenic acids, Diflumethorim, Fludioxonil, Simoxanil, Dimethomolph, Mildiomycine, and the like.

Likewise, examples of insecticides included in the present invention are Furathiocalp, Oxamil, Tralomethrin, Fenpropathrin, Phenvalerate, Fluvalinate, Tefluthrin, Thiocyclum, Imidacloprid, Chlorfenapyr, Emamectine-benzoic acid, sodium oleate, Amitraz, Oxidized-phenbutatin, Tebufenpyrad, Pyrimidifen, Miruvemectin, Morantel-tartrate, Carbam-sodium, and the like.

Examples of growth regulators included in the present invention are Fluruprimidol, Prohexadione-calcium, Trinexapak-ethyl, and the like.

Examples of herbicides included in the present invention are Cyhalohopbutyl, Dimethenamid, Tenylchlor, Isoxaben, Tebutyuron, Azimsulfron, Methosulfronmethyl, Cyclosulfamron, Triazifram, Trifluralin, Vesrodin, Imathapyr, Synmethylin, Disoium-Endtal, Penflesate, and the like.

These agroactive ingredients described in the preferred embodiments are generally unstable under the solar light. However, the agroactive ingredients included in the present invention are not particularly limited to these compounds described herein.

The effective process of the present invention is in generating oxygen free radicals according to the irradiation of light, which work as strong oxidizer and make decompose the above-mentioned agroactive ingredients remaining on and inside the foliage of a plant. In particular, the presence of alkali ions coming from carbonate salts and bicarbonate salts is essential for the acceleration of decomposition and inactivation of said agrochemicals.

The composition for being sprayed on the foliage of a plant described in the present invention works as a photosynthesis accelerator, a plant growth regulator, a resistance donator toward damage of plants, and a decomposer as is set forth in detail hereinbefore. It may be also expected that the composition exhibits more than two effects selected from the group consisting of a photosynthesis accelerator, a plant growth regulator, a disease-resistance donator, and a decomposing agent depending upon the kind of plant and the application conditions.

In a preferred embodiment of the present invention, the ratio of semiconductor photocatalyst(s) to a composition for being sprayed on the foliage of a plant according to the present invention is, preferably from 0.0005% to 50% by weight, more preferably from 0.005% to 10%, and most preferably from 0.05% to 1%. The ratio of less than 0.0005% by weight is undesirable since homogeneous application of said semiconductor photocatalyst(s) on plants at such content is hard to carry out with inconspicuous effects. On the other hand, the ratio of more than 50% by weight leads, upon application to plants, to phyto-toxicities such as chlorosis of foliage, and the like.

In a preferred embodiment of the present invention, the ratio of semiconductor photocatalyst(s) to carbonate salts and/or bicarbonate salts is preferably from 1:20,000 to 1:1 by weight, more preferably from 1:2,000 to 1:3, and most preferably from 1:500 to 1:10. The ratio of carbonate salts and/or bicarbonate salts exceeding 20,000 parts to 1 part of semiconductor photocatalyst(s) per weight is undesirable since it leads, upon application to plants, to the salt damage frequently. On the other hand, the ratio of less than one part to 1 part of semiconductor photocatalyst(s) per weight is also undesirable since the photo-decomposition activity of water is lowered in such condition.

In a preferred embodiment of the present invention, the preferred example of semiconductor photocatalyst(s) is titanium oxide. Titanium oxide is superior in the safety, stability and cost-performance, and thus is easy to use compared to other semiconductor photocatalyst(s). Examples of titanium oxide species in a preferred embodiment of the present invention include titanium dioxide, and its analogs which are generally referred to as water-containing titanium oxide, hydrated titanium oxide, meta-titanic acid, ort-titanic acid, or titanium hydroxide, whereby their crystal forms and production methods are not limited to the examples and descriptions set forth herein. These titanium oxides can be prepared by any method known to public. In one unrestricted example of a preferred embodiment, titanium compounds such as titanium sulfate, titanium chloride or an organo-titanium compound are mixed with alkali, then neutralized. In another example, titanium chloride or organo-titanium compound is oxidized in the gaseous phase, in which addition of calcination process is also allowable.

Titanium oxide in a preferred embodiment of the present invention can take any form without limited by the examples and descriptions set forth herein. For example, it may be a powder or a sol of 5–40% content containing sulfuric acid, hydrochloric acid, or other appropriate dispersing agents. Typical examples of commercially available powdered titanium oxide are ST-1 and ST-31 provided by Ishihara Techno Company, P25 by Nippon Aerosil Company, SSP-25, SSP-20, and SSP-M by Sakai Chemical Industry Company, PC-101 and PC-102 by Titan Industry Company, AMT-100 and ST-157 by Teika Company, DN-10 and DN-22A by Furukawa Machine & Metals Company, A-100 by Taki Chemical Company, and F-6 by Showa Denko Company.

Concerning the commercially available sol products of titanium oxide, STS-01, STS-02 and STS-21 provided by Ishihara Techno Company, CBS and CBS-M by Sakai Chemical Industry Company, H-40, N-40 and CA-40 by Taki Chemical Company, Titania Sol by Teika Chemical Company, and FS-1 and FS-1o by Furukawa Machine & Metals Company may be employed.

Furthermore, it is included in the scope of the present invention to dope metals such as platinum, gold, silver, copper, palladium, rhodium, ruthenium and/or metal oxides such as ruthenium oxide and nickel oxide on the surface of titanium oxide for the purpose of promoting the photocatalytic effect. Treating with an ionized gas like plasma is also allowable. The above compounds may be employed singly or in a mixed form of more than two substances.

In a preferred embodiment of the present invention, titanium oxide explained hereinbefore is preferably in the form of anatase. Anatase-type titanium oxide has a photo-decomposition efficiency higher than rutile-type titanium oxide, and thus is preferred. In the unit crystal lattice of anatase, the unit of titanium oxide is placed one-directionally in four units, while in the unit lattice of rutile, it is placed in two units with closer distance non-directionally. For this reason, the anatase-type has a better electrically reactive property to water on its crystal surface, and is advantageous for carrying out the photo-decomposition reaction of water.

In a preferred embodiment of the present invention, the average particle size of titanium oxide explained hereinbefore is preferably from 1 nm to 500 µm, more preferably from 1 nm to 1 µm, most preferably from 5 nm to 100 nm. Products with average particle size of less than 1 nm are hard to manufacture technically at present. On the other hand, products with average particle size of more than 500 µm are also undesirable as they are frequently associated with troubles such as blocking of spraying nozzles when used in an actual farm as well as their inferior photocatalytic efficiencies.

In a preferred embodiment of the present invention, the above-mentioned carbonate salts and/or bicarbonates salts are preferably to be soluble in water. When using these salts, a quality to form ionic species readily in water is preferred so as to promote said photo-decomposition reaction of water. Carbonate salts and/or bicarbonate salts may be used singly and in combination with two species or more at optional ratio.

In a preferred embodiment of the present invention, the carbonate salts and/or bicarbonates salts are preferably selected from the group consisting of $Na_2CO_3$, $NaHCO_3$, $K_2CO_3$ and $KHCO_3$. They can be used without difficulty whether they are in the form of anhydrates or hydrates. They may be used singly and in combination with two species or more at optional ratio.

In an application of the titled composition for being sprayed on the foliage of a plant described in this invention, it is generally sprayed on the aboveground part of plants. Application methods for the purpose are not limited to the examples and descriptions set forth herein; it can be sprayed, immersed, or applied. In a preferred embodiment, a composition according to the present invention is dispersed in water and sprayed employing powered spraying machine, shoulder-type spraying machine, broadcaster, sprayer, helicopter with or without driver, fuming machine, hand-sprayer, and the like with a ratio of 0.5 to 300 litter per 10 ares.

In a similar context, application of a composition according to the present invention is effective both at the seedling period and the growth period after transplanted to an actual farm when it is sprayed, immersed, or coated on the aboveground part of a plant. However, immersing or coating process after transplantation yields some problems in the work as well as the economic disadvantages. Therefore, spraying on the aboveground part of the plant is preferred.

In a preferred embodiment of the present invention, the periodic application cycle is preferably from 3 to 14 days in accommodation with the growing cycle of new foliage. Depending on the state of growth stage, plant species, and growing degree, however, it may be applied every day or at long intervals.

In a preferred embodiment of the present invention for the spraying amount, the following method is illustrated as a preferred example. In a case of rice plants, a composition for being sprayed on the foliage of a plant according to the present invention is dispersed in water and sprayed on seedlings of rice at a ratio of 10–2,000 ml per one box of seedlings. Treatment of less than 10 ml in the above condition is undesirable as the effects of the composition become insignificant. Treatment exceeding 2,000 ml is also undesirable as the seedlings are often plagued by excess damp. The dispersed composition is preferably sprayed at 100–1,000 ml per one box of seedlings, more preferably at 300–800 ml. In the case of sprinkling on a main farm, it is usually sprayed at 1–500 L per 10 ares, preferably at 10–300 L, more preferably at 50–200 L.

One of the most preferable treatments is to spray the above dispersed composition at a ratio of 500 ml per one box of seedlings every five days starting from the period of 1.5 leaf in the seedling period, and then to process at a ratio of 100 L per 10 ares every ten days after they are transplanted.

In the detailed description of the present invention, the composition for being sprayed on the foliage of a plant according to the invention is preferably sprayed on plants in a water-dispersed form at a dilution ratio less than the upper limit of 100,000 times, more preferably at 5–10,000 times, most preferably at 10–1,000 times. The composition according to the present invention may be processed on the aboveground part of a plant without diluting in water. In that case, however, there arises a problem of drift, which suggests preferably addition of anti-drift agents such as sodium polyacrylate, alginic acid, and various water-soluble polymeric compounds. Dilution of the composition for being sprayed on the foliage of a plant described in the present invention exceeding 100,000 times leads to insignificant effects and is undesirable. Furthermore, dilution exceeding 100,000 times results in non-uniform distribution of said semiconductor photocatalyst(s) particles on the foliage after spraying, and thus is undesirable.

The composition for being sprayed on the foliage of a plant described in the present invention is preferably admixed with adjuvant(s) selected from the group consisting of a nonionic, anionic, cationic, or amphoteric surface active agent, a fixing agent, a thickener, a suspending agent, a neutralizer, an antiseptic agent, and an extending agent singly or in a mixed form, and then applied on plants.

The scope of the adjuvant(s) employed in the present invention is not limited to the examples and descriptions set forth herein and may be used without difficulty unless they effect to hinder the composition for being sprayed on the foliage of a plant described in the present invention.

Examples of anionic surface active agents used for the purpose of this invention include; alkylsufosuccinic acid salts, condensed phosphoric acid salts, alkylbenzenesulfonic acid salts such as sodium dodecylbenzenesulfonate, alkyl-naphthalenesulfonic acid salts, formalin condensates of naphthalenesulfonic acid salts, ligninsulfonic acid salts, salts of polycarboxylic acids, salts of alkylethersulfuric acids, salts of poly-oxyethylene-alkylarylphenylether-sulfuric acids, salts of poly-oxyethylene-alkylarylether-sulfuric acids, salts of poly-oxyethylene-alkylarylsulfuric acids, salts of poly-oxyethylene-alkylarylphenylether-sulfuric acid esters, and salts of poly-oxyethylene-alkylarylphenylether-acetic acid ester-sulfuric acids. With regard to the preferred form of salts, salts of alkali metals, ammonium salts and amine salts may be recommended.

Furthermore, examples of nonionic surface active agents include; poly-oxyethylene-alkylether, poly-oxyethylene-alkylarylether, poly-oxyethylene-alkylarylphenylether, poly-oxyethylene-styrylphenylether, poly-oxyethylene-alkylarylester, sorbitan alkyl ester, poly-oxyethylene-sorbitanalkylester, and poly-oxyethylene-poly-oxypropylene-glycol. It is also allowable to employ a cationic or an amphoteric surface active agent on necessity.

Examples of fixing agents used for the purpose of this invention include; D-sorbitol, paraffin, lime caseinate, silicone, various starches, powder of resins, water-swelling polymers, and the like.

Examples of thickeners used for the purpose of this invention include; water-soluble polymeric compounds such as xanthane gum, gua-gum, carboxylmethylcellulose sodium salt, colloidal silica, alpha-form starch as well as high purity bentonite, hydrophilic silica, and the like.

Examples of suspending agents used for the purpose of this invention include; anionic wetting or dispersing agents such as sodium alkylnaphthalenesulfonate, formalin condensates of sodium alkylnaphthalenesulfonate, sodium ligninsulfonate, and the like, nonionic wetting or dispersing agents such as poly-oxyethylene-poly-styrylphenylether, poly-oxyethylene-nonylphenylether, and the like.

Examples of neutralizers used for the purpose of this invention include sulfuric acid, hydrochloric acid, sodium hydroxide, potassium hydroxide, and the like.

Examples of antiseptic agents used for the purpose of this invention include; aqueous solution of formalin, sodium benzoate, potassium sorbinate, esters of parahydroxybenzoic acid, 1,2-benzthiazoline-3-one, and the like.

Examples of extending agents used for the purpose of this invention include; powdery carriers such as clay, talc, calcium carbonate, diatom earth, zeolite, bentonite, acidic clay, Atavalgus clay, granular carriers such as vermiculite, pearlite, pumice, and miscellaneous substances such as white carbon, potassium chloride, ammonium sulfate, sodium sulfate, powdery cellulose, starch, dextrin, sugar, rice bran, oil cake, corn feed, wheat bran, and the like.

It is also effective to add antifoaming agents such as silicone, antifreezes such as ethylene glycol or propyleneglycol to a composition described in the present invention for being sprayed on the foliage of a plant. They may be employed singly or in combination with two species or more at optional ratio.

It is preferred to admix at least one sort of Hill oxidant to a composition described in the present invention for being sprayed on the foliage of a plant at its practical application to plants. Note that Hill Reaction is defined as a photochemical generation reaction of oxygen by a standard sample of isolated chloroplast (Proc. Roy. Soc. B, 127, 192 (1939)). An oxidant that promotes the reaction is referred to as a Hill oxidant.

Typical examples of Hill oxidants include;
(1) a phosphate-buffered solution (pH 7.5) containing potassium oxalate (0.5 M), ferric ammonium iron sulfate (0.01 M), potassium ferricyanate (0.02 M) and sucrose (0.2 M),
(2) potassium ferricyanate (singular use),
(3) p-benzoquinone,
(4) indophenol-based dyes such as phenol-indophenol or 2,6-dichlorophenol-indophenol,
(5) quinones such as 1,2-naphthoquinone, 1,2-naphthoquinone-4-sulfonate or 1,2-naphthoquinone-2-sulfonate,
(6) aldehydes such as benzaldehyde or salicylaldehyde,
(7) water-extract of yeast or chloroplast.
They may be employed singly or in combination with two species or more at optional ratio.

Embodiments

While the illustrative embodiments of the present invention will be described with particularity hereafter, it will be understood that the scope of the claims appended hereto is not limited to the examples and descriptions set forth herein.

EXAMPLE 1

A composition (1) for being sprayed on the foliage of a plant according to the present invention was prepared, which contained 0.1% by weight of anatase-type titanium oxide (product of Sakai Chemical Industry Company, SSP-25) and 99.9% of water.

EXAMPLE 2

Another composition for being sprayed on the foliage of a plant according to the present invention was prepared, which was shown to have a following composition Composition

|  | Wt % |
| --- | --- |
| anatase-type titanium oxide (Sakai Chemical SSP-25) | 0.5 |
| sodium bicarbonate (Wako Chemical) | 30.0 |
| xanthane gum (thickener) | 0.2 |
| ethylene glycol (antifreeze) | 5.0 |
| formalin solution (antiseptic) | 0.1 |
| extract of yeast cake (Hill oxidant*) | 1.0 |
| water | 63.2 |

The above extract of yeast cake (shown with *) was prepared by the following method.

As a preculture, a sample of yeast (saccharomyces cerevisiae IFO-0324) in one platinum lug was inoculated into a culture solution containing Yeast Nitrogen Base (Difco) in 50 ml of 1% (wt/v) Glucose, kept at 27° C. under agitation overnight. The resultant solution was again inoculated into 950 ml of culture solution having the same composition, and brought to the main culture under the same condition. When the culture was completed, the resultant solution was brought to the centrifugal separation at 2,000 rpm for 5 minutes. The precipitate (yeast cake) was removed of supernatant liquid, suspended in sterilized distilled water under vigorous agitation, and again brought to the centrifugal separation under the same condition. This process was repeated by three times, and the final product was carefully washed to be free from the culture solution. A wet sample (wet weight: 20 g) of the above yeast cake was suspended in 50 ml of 50% (wt/v) ethanol, and brought to the self melt at 30–40° C. under agitation overnight. The resultant suspension was filtered with a membrane filter possessing pores of 0.45 $\mu$m. The filtrate was dried by the spray-drying method to obtain the final extract of yeast.

EXAMPLE 3

Another composition for being sprayed on the foliage of a plant according to the present invention was prepared removing sodium bicarbonate from the composition in EXAMPLE 2 and adding equivalent water.

EXAMPLE 4

A composition for being sprayed on the foliage of a plant according to the present invention was prepared removing the yeast component from the composition in EXAMPLE 2 and adding equivalent water.

COMPARATIVE EXAMPLE 1

A composition for being sprayed on the foliage of a plant according to the present invention was prepared removing anatase-type titanium oxide from the composition of EXAMPLE 2 and adding equivalent water.

(Test 1)

Measurements were carried out for the active oxygen species evolving from the composition (1) under the irradiation of light. The definition of active oxygen species varies depending on the literature. In a narrowed definition, it indicates a compound where the ordinary oxygen taking the electron configuration of triplet ground state ($^3O_2$) is elevated to an excited state possessing a higher reactivity. Typical examples of the active oxygen species are shown to be the next five; superoxide anion radical ($.O_2^-$), hydroperoxide radical ($.OOH$), hydrogen peroxide ($H_2O_2$), hydroxy radacal ($.OH$) and singlet oxygen ($^1O_2$).

The measuring methods of the active oxygen species include; direct methods such as the electrode method, the UV spectrum method, and the ESP method (pH-Jump), indirect methods such as the cytochrome method, the NBT method, the chemical luminescence method, the fluorescence method and the TNM reduction method. Since the species like ($.O_2^-$) and ($.OH$) have a very short life (high reactivity), and are not suited to the direct method in most cases. For the reason, the measurement of the active oxygen species in this test was performed with the ESP (electron spin resonance)—spin trap method (an indirect method) as it yields reliable results in high sensitivity as well as good reproducibility. For trapping the oxygen free radicals employed were a group of nitrons, typically DMPO (5,5-dimethyl-1-pyrroline-1-oxide) and PBN (α-Phenyl-N-t-butylnitrone). The former was selected as the trapping agent in the present test as it has a high solubility in water and a high trapping rate, and allows facile recognition of the radical species.

Measuring method: For the ESP spectrometer, RE-3X (product of Nippon Densi Company) was employed. The measuring conditions are shown in Table 1.

TABLE 1

| Temperature | 20° C. |
|---|---|
| Power | 5 mW |
| Center Field | H = 333.5 mT(militesla) |
| Sweed Width | ΔH = 5 mT |
| Field Modulation Width | Modulation = 0.1 mT |
| Receiver Gain | Amp. = 200 |
| Time Constant | Response = 0.1 sec |

In the above test DMPO (5,5-dimethyl-1-pyrroline-1-oxide, product of Labotec Company) was employed as the spin-trapping agent, and a flat cell (LLC04A, product of Labotec) for use with aqueous solution was adopted. In a preferred embodiment, 185 μl of the composition (1) for being sprayed on the foliage of a plant in EXAMPLE 1 was taken out by a micro pipette and transferred into a tube, added with 15 μl of purified DMPO, and mixed thoroughly. A measuring cell was filled with this solution, fixed onto the cavity of the measuring apparatus, and brought to the measurement at the condition described in Table 1. The measurement was performed under the irradiation of light to the cell powered by a xenon lamp (product of Ushio Electric Company, type; UI-501C) installed within its cavity. The result is shown in FIG. 1.

Figure 2:
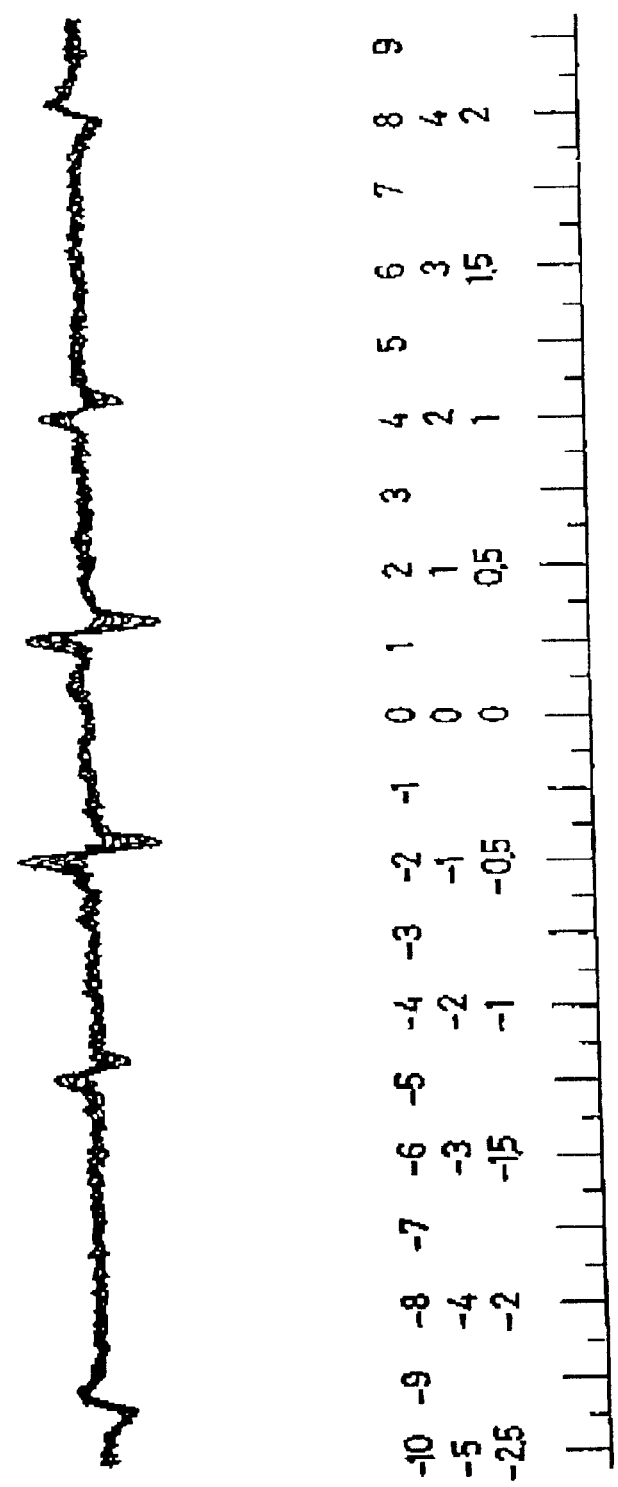
FIG. 2 shows an ESR-spectrum of each of pure water and DMPO.

For the purpose of investigating the effect of light irradiation with DMPO alone, 185 μl of purified water was taken out by a micro pipette and transferred into a tube, added with 15 μl of purified DMPO, mixed thoroughly, and sent to the measurement at a similar condition. The result is shown in FIG. 2. In each of the measurements, the scanning time was set to 2 minutes, and the changes with the lapse of time were recorded in 8 times successively on a recording paper.

(Results of Test 1 and Discussion)

The test by the composition (1) in FIG. 1 was compared with the test by DMPO alone. For the former, a spectrum typical of the ($.OH$) radical adduct with DMPO was observed inside the third (g2=12.003) and the fourth (g1= 1.9081) signals of the manganese marker with the intensity ratio of 1:2:2:1 (hfs parameter aH=aN=1.49 mT, g-value; 2.0090 (2.005/2.535)). Furthermore, In a comparison with the result of comparative test using purified water and DMPO as shown in FIG. 2, the spectral intensity of the composition (1) for being sprayed on the foliage of a plant according to the present invention, when coupled with DMPO, was shown to be clearly larger. This suggests that the addition of a composition (1) for being sprayed on the foliage of a plant according to the present invention accelerates the photo-decomposition reaction of water much more compared to ordinary water alone.

The above results indicate that the composition (1) for being sprayed on the foliage of a plant according to the present invention is capable of accelerating the photo-decomposition reaction of water. Therefore, the composition for being sprayed on the foliage of a plant described in the present invention is proved to be capable of accelerating formation of ethylene (a plant hormone), formation of phytoalexin (an antibacterial substance), and decomposition of agrochemical ingredients remaining in excess on the foliage of treated plants, due to a fact that it promotes the photosynthetic activity of plants as well as acceleration of the lipid peroxidation in living bodies by the action of active oxygen species.

(Test 2)

In order to investigate the effects of a composition of the present invention for being sprayed on the foliage of a plant in each of Working Examples 2 to 4 and the effects of a composition in Comparative Example 1 on a sugar degree in foliage, a test was carried out.

(Material and Test Procedure)

As crops under test, a tomato, a cucumber and a strawberry were used, all of which were cultivated in a hothouse. As the sort of tomato, "MOMOTARO" was employed, and what were cultivated in a poly-pot till a fifth leaf stage were provided for the test. As the sort of cucumber, "HOKUSHIN" was employed, and what were cultivated in a poly-pot till a third leaf stage were provided for the test. As the sort of strawberry, "NYOHO" was employed, and seedings each of which has four leaves were transplanted at a ratio of three stumps in one planter having a volume of 40 liters, and when a rooting was sufficiently taken after about one month, they were provided for the test.

For the three kinds of crops under test, city water; a five hundred times diluted solution of a composition for being sprayed on the foliage of a plant of the present invention in each of Working Examples 2 to 4; and a five hundred times diluted solution of a composition of Comparative Example 1 were sprayed, respectively, at eight in the morning in a fine weather day at such an amount that the foliages are sufficiently wetted. Then, at a two hours interval after eight in the morning when the test was started, namely, at eight, ten, twelve, fourteen, sixteen and eighteen, a sugar degree of each of the leaves was determined by using a Brix meter (Hand Refracto-meter; Type N-1; Co., Ltd. ATAGO make).

With respect to the effects of the composition for being sprayed on the foliage of a plant of the present invention in each of Working Examples 2 to 4 on a sugar degree of each of the leaves, the results of the third leaf of the tomato, the results of the second leaf of the cucumber, and the results of all of the developed leaves of the strawberry are shown in Tables 2, 3 and 4, respectively.

TABLE 2

Changes in Sugar Degrees in Foliage of Third Leaf of Tomato (Brix Sugar Degree; Unit: %)

|  | 8:00 | 10:00 | 12:00 | 14:00 | 16:00 | 18:00 |
|---|---|---|---|---|---|---|
| Control Plot | 4.8 | 5.6 | 6.9 | 8.0 | 6.9 | 6.0 |
| Working Ex. 2 | 4.9 | 8.6 | 9.5 | 9.4 | 7.8 | 6.3 |
| Working Ex. 3 | 4.7 | 7.3 | 9.0 | 9.0 | 7.4 | 6.1 |
| Working Ex. 4 | 4.8 | 8.0 | 9.3 | 9.2 | 7.7 | 6.2 |

TABLE 2-continued

Changes in Sugar Degrees in Foliage of Third
Leaf of Tomato (Brix Sugar Degree; Unit: %)

|  | 8:00 | 10:00 | 12:00 | 14:00 | 16:00 | 18:00 |
|---|---|---|---|---|---|---|
| Comparative Ex. 1 | 4.9 | 6.1 | 7.3 | 8.3 | 6.9 | 5.9 |

TABLE 3

Changes in Sugar Degrees in Foliage of Second
Leaf of Cucumber (Brix Sugar Degree; Unit: %)

|  | 8:00 | 10:00 | 12:00 | 14:00 | 16:00 | 18:00 |
|---|---|---|---|---|---|---|
| Control Plot | 5.1 | 7.2 | 8.8 | 10.2 | 8.1 | 6.3 |
| Working Ex. 2 | 5.2 | 10.9 | 11.8 | 11.7 | 9.0 | 6.9 |
| Working Ex. 3 | 5.3 | 9.8 | 10.5 | 11.0 | 8.6 | 6.6 |
| Working Ex. 4 | 5.1 | 10.3 | 11.1 | 11.3 | 8.7 | 6.7 |
| Comparative Ex. 1 | 5.2 | 7.8 | 9.0 | 10.3 | 8.6 | 6.5 |

TABLE 4

Changes in Sugar Degrees in Foliage of Developed
Leaves of Strawberry (Brix Sugar Degree; Unit: %)

|  | 8:00 | 10:00 | 12:00 | 14:00 | 16:00 | 18:00 |
|---|---|---|---|---|---|---|
| Control Plot | 4.1 | 4.6 | 5.2 | 5.2 | 4.8 | 4.2 |
| Working Ex. 2 | 4.2 | 5.8 | 5.9 | 6.4 | 6.1 | 4.8 |
| Working Ex. 3 | 4.3 | 5.5 | 5.7 | 6.0 | 5.9 | 4.5 |
| Working Ex. 4 | 4.3 | 5.6 | 5.9 | 6.0 | 5.7 | 4.7 |
| Comparative Ex. 1 | 4.3 | 5.0 | 5.4 | 5.6 | 5.3 | 4.5 |

(Results of Test 2 and Consideration)

By spray-treating the tomatoes, the cucumbers and strawberries with the composition of the present invention for being sprayed on the foliage of a plant in each of Working Examples 2 to 4, a sugar degree in the foliage of each of the plants was elevated. Furthermore, when the composition of the present invention for being sprayed on the foliage of a plant in each of Working Examples 2 to 4 was sprayed, the sugar degree in the foliage was characterized in that it is apt to be elevated from a relatively earlier period, as compared with the one when city water was sprayed. Thereby, it was confirmed that the composition of the present invention for being sprayed on the foliage of a plant in each of Working Examples 2 to 4 is sprayed thereon, the efficiency of photosynthesis in the foliage of a plant is elevated, which leads to the enhancement of the yield of sugar in the foliage per day.

(Test 3)

In order to investigate the effects of a composition of the present invention for being sprayed on the foliage of a plant in each of Working Examples 2 to 4 and the effects of a composition in Comparative Example 1 on the elongation of an adventitious root of a tomato, a test was carried out.

(Material and Test Procedure)

As a sort thereof under test, "HOUSE-MOMOTARO" of Takii & Co., Ltd. make was employed, wherein a forced sprouting treatment of seeds was carried out for a period of three days on Jul. 15, 1998, and thereafter, they were cultivated in a glass room in the Tropical Horticulture Laboratory of Tokyo University of Agriculture. The seeds were sown in a black poly-pot (having a diameter of 9 cm, and a height of 8 cm) on Jul. 18, 1998, and budding occurred on Jul. 20, 1998.

A leaf mould and a tuff-loam depth soil were mixed with each other at a ratio of 1:2 in a poly-pot, and 16 g of lime was added thereto. The tuff-loam depth soil was air-dried, and passed through a sieve of 1 cm square for use. Seedlings as grown into about 10 cm were cut at an 1.5 cm above the ground on Aug. 8, 1998, and then, the seedlings were dipped in city water; a five hundred times diluted solution of a composition of the present invention for being sprayed on the foliage of a plant in each of Working Examples 2 to 4; and a five hundred times diluted solution of a composition in Comparative Example 1, namely, in test solutions for five plots in total, respectively, for a period of ten seconds, while the whole surfaces of test-tubes having a volume of 70 ml were wound with a black vinyl tape and covered with aluminum foil, and thereafter, 60 ml of distilled water was introduced in each of the test-tubes, and of the seedlings of tomatoes were immersed into the test-tubes respectively till about a depth of 1.5 cm from the cut end. Each of the plots had ten repetitions, and was still stood in an environment control room of 2500 lux at a temperature of 20° C., and after seven days, a maximum length of adventitious roots of each of them and the number of the roots thereof were determined.

With respect to the effects of the composition for being sprayed on the foliage of a plant of the present invention in each of Working Examples 2 to 4 and the composition in Comparative Example 1 on the elongation of adventitious roots of tomatoes, the results are shown in Table 5.

TABLE 5

|  | Root Length (cm) | Root Number | Root Weight (g) | (Root Weight)/ (Whole Weight) |
|---|---|---|---|---|
| Control Plot | 3.3 | 34 | 170 | 0.044 |
| Working Ex. 2 | 6.7 | 48 | 238 | 0.069 |
| Working Ex. 3 | 5.8 | 43 | 198 | 0.051 |
| Working Ex. 4 | 6.3 | 47 | 228 | 0.066 |
| Comparative Ex. 1 | 4.0 | 35 | 169 | 0.044 |

(Results of Test 3 and Consideration)

It has been found that the length of root is in the order of Working Example 2>Working Example 4>Working Example 3>Comparative Example 1>Control Plot, and regarding each of the number of roots and the weight of roots, Working Example 2 is superior to Control Plot. Additionally, from the results of [the weight of roots]/[the whole weight], it has been found that in the 500 times plot in Working Example 2, the growth of underground portion is expedited.

Generally, it is known that when a plant is cut, a cell division begins near the cut end. "It is considered that the cell division will be induced by: stimulation by being cut; stimulation by a radical as produced by photo-irradiation onto the composition for being sprayed on the foliage of a plant of the present invention in each of Working Examples 2 to 4; and an action of a phenol substance which hastens the rooting."

It is considered that by providing the plants with the composition for being sprayed on the foliage of a plant of the present invention in each of Working Examples 2 to 4, Phenylalanine Ammino Lylase is activated, and thereby, a phenol substance which hastens the rooting will be produced.

(Test 4)

In order to investigate the effects of application on leaves of the composition of the present invention for being sprayed on the foliage of a plant in each of Working Examples 2 and 4 and the composition in Comparative Example 1 on the production of ethylene in tomato-seedlings, a test was carried out.

(Material and Test Procedure)

A sort thereof under test and a method of cultivation are similar to the ones in Test 1; namely, forced sprouting treatment of seeds were carried out on Sep. 12, 1997, sowing was carried out on Sep. 15, 1997, budding occurred on Sep. 18, 1997, and application on leaves was carried out on Oct. 12, 1997. For treatment, a five hundred times diluted solution of the composition in each of Working Example 2, Comparative Example 1, and Working Example 4 was applied on the foliage of the tomato-seedlings, while in a control plot, city water was sprayed on the foliage. After three days, the amount of ethylene produced was determined.

With respect to a procedure of determination, after three days from the day when application on the foliage was carried out, a third leaf was cut, and then, the leaf was stamped out by using a cork borer having a diameter of 1 cm, while a wet filter paper was spread within a 50 ml-Erlenmeyer flask, and ten pieces of the cut leaf were introduced therein, and thereafter, the Erlenmeyer flask was stoppered with a silicone plug, and the whole of the Erlenmeyer flask was wound with a black vinyl. Furthermore, the Erlenmeyer flask was covered with aluminum foil, and they were incubated at a temperature of 25° C. for a period of six hours so as to provide for determination. In order to determine the amount of ethylene produced, a gas chromatograph (Shimadzu Corp. make; GC-14A) was used, and SUNPACK "A" at a temperature of 80° C. as a column, $N_2$ (6 $kg/cm^2$) as a carrier gas, FID at a temperature of 150° C. as a detector, and an injector at a temperature of 120° C. were employed, and determination for each of the treated plots was repeated three times.

In connection with the effects of application on leaves of the composition of the present invention for being sprayed on the foliage of a plant in each of Working Examples 2 and 4 and the composition in Comparative Example 1 on the production of ethylene in tomato-seedlings, the results are shown in Table 6.

TABLE 6

| | Amount Produced (nl/g/h) |
|---|---|
| Control Plot | 4.1 |
| Working Ex. 2 | 10.9 |
| Working Ex. 43 | 8.8 |
| Comparative Ex. 1 | 4.3 |

(Results of Test 4 and Consideration)

When a five hundred times diluted solution of the composition in each of Working Examples 2 and 4 was applied thereon, the amount of ethylene produced was increased after three days.

It is known that ethylene controls the growth of a plant above the ground, while the growth of root is hastened; and furthermore, ethylene promotes lignification, and decreases cuticle transpiration, and thereby, drought resistance is increased, the invasion of fungus is prevented so that disease resistance is enhanced. According to the tests concerned, it has been suggested that application of a five hundred times diluted solution of the composition in each of Working Examples 2 and 4 onto the foliage of tomatoes can be utilized for raising good seedlings.

Such an action is useful, for example, for decreasing the amount of agricultural chemicals to be used, and furthermore, it has been suggested that it can be utilized for raising good seedlings.

(Test 5)

In order to investigate the effects of the composition of the present invention for being sprayed on the foliage of a plant in each of Working Example 2 on the production of Sakuranetin and Momilactone "A", each of which is Phytoalexin for a rice plant, a test was carried out.

(Material and Test Procedure)

As a sort thereof under test, "Nippon-Bare" was used, which was grown till the age of 3.5 in a paper pot which was filled with a soil as mixed with a complex fertilizer (N:P:K= 10:6:8) of 14 g, and then transplanted at a ratio of three per $\frac{1}{5000}$ a Wagner-pot. As a basal fertilizer, a complex fertilizer (N:P:K=10:6:8) of 7 g was provided in the form of fertilizer incorporation to plow layer, and the rice plants had been cultivated till a sixth leaf stage in a green-house, and then, fifth leaves of the rice plants were provided as experimental materials.

The fifth leaves were cut to an even length of 20 cm, and a cut having a diameter of 1 mm was made at the center area of each of the fifth leaves at intervals of 10 mm, while a Kim-wipe as wetted with distilled water was spread within a plastic container. Then, each of the fifth leaves was placed so that the upper side of the leaf will be upward. Thereafter, a one hundred diluted aqueous solution of the composition of the present invention for being sprayed on the foliage of a plant in Working Example 2 was applied to the cut having a diameter of 1 mm on the leaf at a ratio of 25 μl per cut, and the container was covered with a transparent lid, and was incubated at a temperature of 25° C. under a light condition for a period of sixty hours. Besides, in a similar manner thereto, as a control plot, a plot in which distilled water was applied thereto at a ratio of 25 μl per cut was provided. After sixty hours, a test liquid as left on the surface of the leaf, and the leaf as stamped out into a diameter of 10 mm centering around the cut by using a cork borer were subjected to extraction with 70% hot methanol, and subjected to vacuum concentration, and thereafter, a water phase was taken out, which was further subjected to extraction with diethyl ether, the ether phase was taken out, and thereafter the ether phase was concentrated and dried and solidified. Thereafter, it was passed through a normal phase TLC (benzene:ethyl acetate-:formic acid=10:1:1), and what was eluted with ethyl acetate was concentrated and dried and solidified, and Sakuranetin was determined from a reverse phase HPLC (methanol including 0.2 N of formic acid: solvent "A"=6:4, wherein solvent "A" includes 2 g of $NaNO_3$ and 0.05 g of $H_2SO_4$ per 100 ml of $H_2O$). On the other hand, it was passed through BOND ELUT C18, and Momilactone "A" was determined from what was eluted with 80% methanol by using GC-MS/ SIM.

In connection with the amounts of Sakuranetin [whose structural formula is represented by the formula (1)] and Momilactone "A" [whose structural formula is represented by the formula (2)] as produced in each of the plots, the results are shown in Table 7.

[Chemical Form. 1]

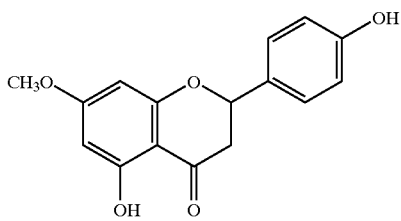

Formula (1)

[Chemical Form. 2]

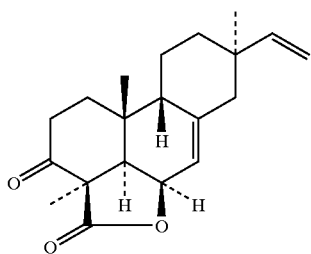

Formula (2)

TABLE 7

| | Amount of Sakuranetin Produced | Amount of Momilactone "A" Produced |
|---|---|---|
| Control Plot | n. d | n. d |
| Working Ex. 2 | 459.10 | 61.33 |

(Results of Test 5 and Consideration)

In the plot for Working Example 2, Sakuranetin of 459.10 ng/spot per cut and Momilactone "A" of 61.33 ng/spot per cut were determined, and thus, by treating the plants with the composition for being sprayed on the foliage of a plant of the present invention in Working Example 2, antibacterial activity was remarkably increased.

Figure 3:
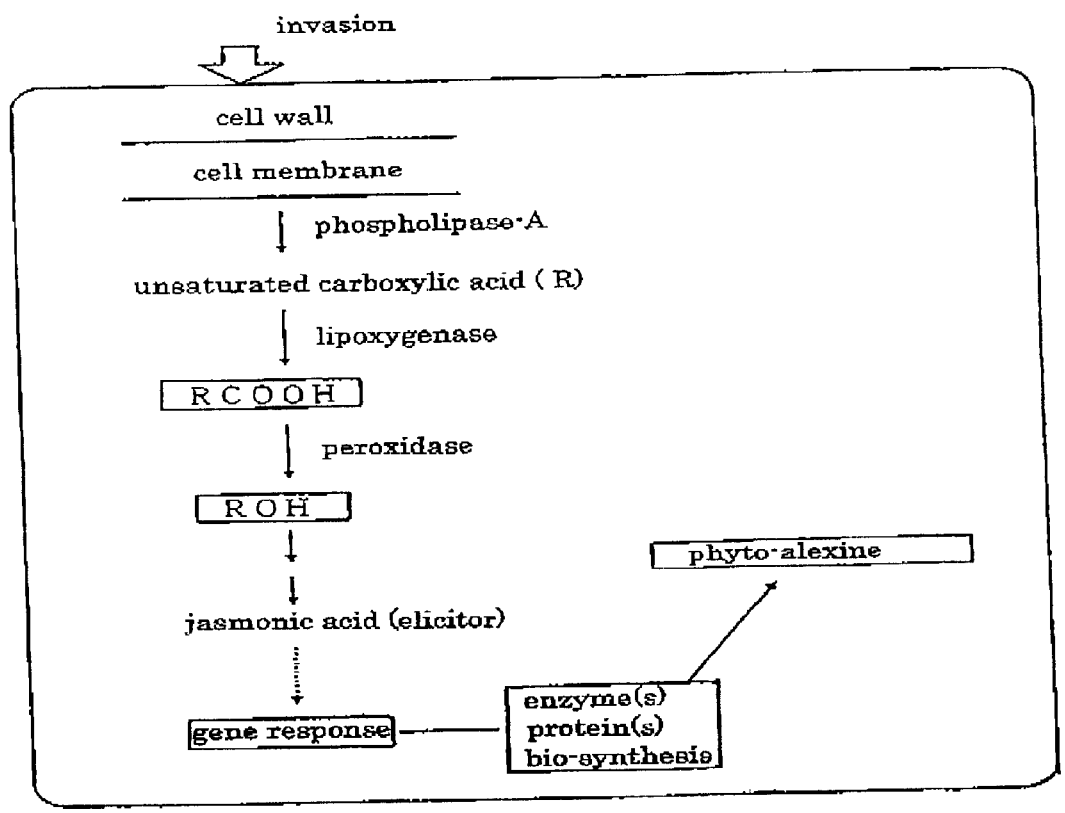
FIG. 3 illustrates a dynamic protection mechanism against a plant disease-causing bacteria such as a blast bacteria of a rice plant.

Generally, Sakuranetin and Momilactone "A", each of which is Phyto-alexin for a rice plant, are known as a dynamic defensive substance to rice plant blast (refer to FIG. 3), and is important to act so as to prevent rice plant blast from invading. According to the results of the test concerned, it is suggested that the treatment with the composition for being sprayed on the foliage of a plant of the present invention in Working Example 2 can be utilized for preventing rice plant blast.

(Test 6)

In order to investigate the effects of application on the foliage of the composition of the present invention for being sprayed on the foliage of a plant in each of Working Example 2 on the occurrence of rice plant blast (or *Pyricularia oryzae*), a test was carried out.

(Material and Test Procedure)

As a sort thereof under test, "KOSHIHIKARI" was used, which was grown till the age of 3.5 in a paper pot which was filled with a soil as mixed with a complex fertilizer (N:P:K= 10:6:8) of 14 g, and then transplanted at a ratio of three per 1/5000 a Wagner-pot. As a basal fertilizer, a complex fertilizer (N:P:K=10:6:8) of 7 g was provided in the form of fertilizer incorporation to plow layer, and the rice plants had been cultivated till an eighth leaf stage in a green-house, and then, they were provided as experimental materials. As a pretreatment, the composition of the present invention for being sprayed on the foliage of a plant in Working Example 2 was diluted with distilled water by one hundred times, and the solution was sprayed on the foliage at a ratio of 100 ml per pot. Furthermore, in the control plot, in a similar manner thereto, distilled water was sprayed on the foliage at a ratio of 100 ml per pot. After 24 hours from the pretreatment, the whole surface above the ground was inoculated with a rice blast bacterium (virus), and the total of a necrosis portion and a disintegration portion per $cm^2$ of the surface of a leaf having a lesion which was occurred after 10 days from the inoculation was evaluated by an area ratio. First, the whole area of the leaf was measured by using a leaf area meter, and then, a lesion portion was introduced into an image analyzer through a microscope for determination, and thereby, the evaluation was made.

The results of each of the plots are shown in Table 8.

TABLE 8

| | Control Plot | Treated Plot of Working Ex. 2 |
|---|---|---|
| Necrosis Ratio (%) | 18.9 | 2.5 |

(Results of Test 6 and Consideration)

A necrosis ratio of the control plot was 18.9%, while the one of the plot as treated with a one hundred times diluted solution of the composition of the present invention for being sprayed on the foliage of a plant in Working Example 2 was 2.5%, which is a value of about one seventh. It is considered that due to the treatment with a one hundred times diluted solution of the composition of the present invention for being sprayed on the foliage of a plant in Working Example 2, the production of Phyto-alexin was promoted, and thereby bacteria (or virus) was prevented from invading so as to enhance disease resistance.

(Test 7)

In order to investigate the effects of application on the foliage of the composition of the present invention for being sprayed on the foliage of a plant in each of Working Example 2 on the yield of a rice plant, a test was carried out.

(Material and Test Procedure)

As a sort thereof under test, "HITOMEBORE" was used, and a test was carried out at a test field in Onda District, Miyagi Prefecture. Rice-planting was carried out by using seedlings at a 2.5 leaf stage on May 7, 1997, with an interrow space of 33 cm and a stump space of 15 cm, and a non-treated plot, and a plot as treated with a one thousand times diluted solution of the composition of the present invention for being sprayed on the foliage of a plant in each of Working Example 2 were provided by 30 square meters, respectively. The one thousand times diluted solution of the composition of the present invention for being sprayed on the foliage of a plant in each of Working Example 2 was sprayed on Jun. 22, 1997 (a tillering stage), Jul. 6, 1997 (before a time of differentiation of young ears), Jul. 14, 1997 (a stage of the formation of young ears), and Aug. 13, 1997 (after five days from the formation of ears), namely by four times in total. An investigation was carried out on Sep. 20, 1995. For the investigation, all of the rice plants in each of the plots were reaped. In order to investigate the yield per ten ares, the total weight above the ground, the weight of straw, the weight of unhulled rice, the weight of coarse unpolished rice, the weight of crushed rice, the weight of refined unpolished rice, the weight of one thousand of grains, and the moisture were determined. Furthermore, dominant ears of thirty pieces were selected from a typical stump in each of the plots, and thereafter, the total number of grains, the number of whole grains, the number of empty grains, and the number of crushed rice were researched in order to investigate stumps.

The results of the yield investigation are shown in Table 9, and the results of the stumps investigation are shown in Table 10.

TABLE 9

|  | Non-Treated Plot | Treated Plot of Working Ex. 2 |
|---|---|---|
| Total Weight (kg) | 1417 | 1585 |
| Straw Weight (kg) | 693 | 754 |
| Unhulled Rice Weight (kg) | 724 | 831 |
| Coarse Unpolished Rice (kg) | 572 | 673 |
| Crushed Rice (kg) | 88.9 | 64.9 |
| Refined Unpolished Rice (kg) | 483.1 | 608.1 |
| Weight of One Thousand of Grains (g) | 22.2 | 22.4 |
| Moisture (%) | 14.9 | 15.0 |

TABLE 10

|  | Total Number of Grains | Number of Whole Grains | Number of Empty Grains | Number of Crushed Rice |
|---|---|---|---|---|
| Non-Treated Plot | 85.9 | 62.9 | 7.1 | 15.9 |
| Treated Plot of Working Ex. 2 | 95.0 | 86.0 | 3.1 | 5.9 |

[Effects of the Invention]
(Results of Test 7 and Consideration)

According to the results of the yield investigation, as compared with the weight of refined unpolished rice in the non-treated plot, the one in the treated plot was of 125%, namely, showed an increased yield of twenty percent. Furthermore, according to the results of the stumps investigation, both the total number of grains and the number of whole grains in the treated plot were larger, while both the number of empty grains and the number of crushed rice were smaller.

From the above-mentioned results, it has been demonstrated that by spraying the composition of the present invention for being sprayed on the foliage of a plant in Working Example 2 on the foliage, the number of set grain is increased, and a yield rate is enhanced, which leads to an increased yield. Besides, it has been confirmed that the rate of occurrence of blast in a field of the treated plot in the hot season was still lower controlled, whose accurate investigation was not achieved. Thus, it is guessed that the fact that the infection rate of blast was decreased by the above treatment led to an increased yield.

(Effects of the Invention)

By using a composition for being sprayed on the foliage of a plant of the present invention, carbon dioxide assimilation in a plant can be expedited. Furthermore, by using the composition for being sprayed on the foliage of a plant, an oxygen free radical as produced in a process of a photodecomposition reaction of water can be used for a lipid peroxidation reaction in a plant cell membrane, and the production of ethylene, which is one of plant hormones, is expedited, and consequently, the plant growth such as the dwarf of the plant, the promotion of rooting in a capillary root thereof, the promotion of date of maturity, the formation of an abscission layer, or the induction of flower bud can be controlled. Furthermore, by using the composition for being sprayed on the foliage of a plant, Phyto-alexin, which is derived by a lipid peroxidation reaction is accumulated, and thereby a disease resistance for the plant can be provided. Besides, by using the composition for being sprayed on the foliage of a plant, a bactericide, an insecticide, a growth regulator and/or a herbicide which are excessively left on the surface of the foliage can be decomposed.

A composition for being sprayed on the foliage of a plant of the present invention is, for example, suspended in water, and is applied to foliage which is a ground portion of a plant, by using a sprayer or the like, and thereby, the above-mentioned effects can be provided.

What is claimed is:

1. A method for enhancing the sugar degree in a foliage of a plant, which comprises spraying a composition comprising at least one semiconductor photocatalyst, at least one Hill oxidant and an aqueous solution of at least one compound selected from the group consisting of carbonates and hydrogencarbonates onto a foliage of said plant.

2. The method according to claim 1 wherein said compound is selected from the group consisting of $Na_2CO_3$, $NaHCO_3$, $K_2CO_3$ and $KHCO_3$.

3. The method according to claim 1 wherein said semiconductor photocatalyst is a titanium oxide.

4. The method according to claim 3, said titanium oxide is of anatase-type.

5. The method according to claim 3, said titanium oxide has an average particle size of 1 nm to 500 μm.

* * * * *